United States Patent
Patil et al.

(10) Patent No.: US 10,746,676 B2
(45) Date of Patent: Aug. 18, 2020

(54) METHOD FOR THE MANUFACTURE OF POLY(ALIPHATIC ESTER-CARBONATE)S AND USES THEREOF

(71) Applicant: SABIC GLOBAL TECHNOLOGIES B.V., Bergen Op Zoom (NL)

(72) Inventors: Rahul Patil, Mount Vernon, IN (US); Shankar Kollengodu Subramanian, Mount Vernon, IN (US); James Franklin Hoover, Mount Vernon, IN (US); Guangxin Lin, Mount Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 38 days.

(21) Appl. No.: 16/318,637

(22) PCT Filed: Dec. 19, 2016

(86) PCT No.: PCT/US2016/067513
§ 371 (c)(1),
(2) Date: Jan. 17, 2019

(87) PCT Pub. No.: WO2018/017150
PCT Pub. Date: Jan. 25, 2018

(65) Prior Publication Data
US 2019/0277785 A1  Sep. 12, 2019

Related U.S. Application Data

(60) Provisional application No. 62/364,564, filed on Jul. 20, 2016.

(51) Int. Cl.
| | |
|---|---|
| C08G 63/64 | (2006.01) |
| G01N 24/08 | (2006.01) |
| C08G 63/91 | (2006.01) |
| C08G 64/16 | (2006.01) |
| C08G 64/24 | (2006.01) |
| C08G 64/42 | (2006.01) |
| G01N 33/44 | (2006.01) |
| C08G 63/79 | (2006.01) |

(52) U.S. Cl.
CPC .......... *G01N 24/088* (2013.01); *C08G 63/64* (2013.01); *C08G 63/79* (2013.01); *C08G 63/916* (2013.01); *C08G 64/1608* (2013.01); *C08G 64/24* (2013.01); *C08G 64/42* (2013.01); *G01N 33/442* (2013.01)

(58) Field of Classification Search
USPC ........................................ 528/196, 198, 199
See application file for complete search history.

(56) References Cited

U.S. PATENT DOCUMENTS

| | | |
|---|---|---|
| 5,274,068 A | 12/1993 | Boden et al. |
| 6,117,968 A | 9/2000 | Davis et al. |
| 2015/0301466 A1 | 10/2015 | Moffat et al. |

FOREIGN PATENT DOCUMENTS

| | | |
|---|---|---|
| EP | 0433716 A2 | 6/1991 |
| WO | 2016011332 A1 | 1/2016 |

OTHER PUBLICATIONS

Chan et al.; "Facile Quantitative Analysis of Hydroxyl End Groups of Poly(2,6-dimethyl-1,4-phenylene Oxide)s by 31P NMR Spectroscopy"; Macromolecules; 27; pp. 6371-6375; (1994).
International Search Report and Written Opinion; International Application No. PCT/US2016/067513; International Filing Date Dec. 19, 2016; dated Jun. 16, 2017; 18 pages.
Spyros et al.; A Study of Poly(hydroxyalkanoate)s by Quantitative 31P NMR Spectroscopy: Molecular Weight and Chain Cleavage; Macromolecules; 30; pp. 327-329; (1997).
Spyros, A.; "Quantitative Determination of the Distribution of Free Hydroxylic and Carboxylic Groups in Unsaturated Polyester and Alkyd Resin by 31 P-NMR Spectroscopy"; Journal of Applied Polymer Science; 83(8); pp. 1635-1642; (2001).

*Primary Examiner* — Terressa Boykin
(74) *Attorney, Agent, or Firm* — Cantor Colburn LLP

(57) ABSTRACT

An interfacial process for preparing a poly(aliphatic ester-carbonate) includes providing an initial polymerization reaction mixture comprising an aliphatic C6-20 dicarboxylic acid, a bisphenol, an alkali hydroxide, and optionally a catalyst in a solvent system comprising water and an immiscible organic solvent, adding an initial portion of a carbonyl dihalide over a first time period while maintaining the reaction at a first pH from 7 to 8; and adding a second portion of the carbonyl dihalide over a second, subsequent time period while maintaining the reaction pH at a second pH from 9 to 12, to provide a product polymerization mixture, wherein the amount of alkali hydroxide in the initial polymerization reaction mixture is effective to increase the fraction of the first time period at a measured pH of 7 to 8 compared to the same reaction mixture with a higher amount of alkali hydroxide in the initial polymerization mixture.

19 Claims, No Drawings

METHOD FOR THE MANUFACTURE OF POLY(ALIPHATIC ESTER-CARBONATE)S AND USES THEREOF

CROSS REFERENCE TO RELATED APPLICATIONS

This application is a National Stage application of PCT/US2016/067513, filed Dec. 19, 2016, which claims the benefit of U.S. Provisional App. Ser. No. 62/364,564, filed Jul. 20, 2016, both of which are incorporated by reference in their entireties herein.

BACKGROUND

Poly(aliphatic ester-carbonate)s are high flow, ductile materials that are particularly useful in manufacturing articles by injection molding. Poly(aliphatic ester-carbonate)s are generally manufactured from aliphatic dicarboxylic acid and bisphenol comonomers, and a carbonyl source by a two-stage interfacial process. A strong alkali base is present to aid dissolution of the comonomers in the two-phase reaction medium, and the carbonyl source is introduced in two stages, a first lower pH stage, followed by a second, higher pH stage. There remains a need in the art, however, for improved methods for the manufacture of poly(aliphatic ester-carbonate)s, particularly methods that can produce copolymer with high throughput. It would be useful if the methods could be adapted to produce poly(aliphatic ester-carbonate)s having one or more new or improved properties, such as improved hydrostability.

BRIEF DESCRIPTION

An interfacial process for preparing a poly(aliphatic ester-carbonate) comprises
providing an initial polymerization reaction mixture comprising an aliphatic $C_{6-20}$ dicarboxylic acid, a bisphenol, an alkali hydroxide, and optionally a catalyst, in a solvent system comprising water and an immiscible organic solvent,
adding an initial portion of a carbonyl dihalide over a first time period while maintaining the reaction at a first pH from 7 to 8; and
adding a second portion of the carbonyl dihalide over a second, subsequent time period while maintaining the reaction pH at a second pH from 9 to 12, to provide a product polymerization mixture comprising the poly(aliphatic ester-carbonate),
wherein the amount of alkali hydroxide in the initial polymerization reaction mixture is an amount effective to increase the fraction of the first time period at a measured pH of 7 to 8 compared to the same reaction mixture with a higher amount of alkali hydroxide in the initial polymerization mixture.

A poly(aliphatic ester-carbonate) is made by the foregoing method.

An article subject to conditions of heat and humidity comprises the poly(aliphatic ester-carbonate) composition made by the method above, preferably a medical article, a food preparation, storage, or consumption article, a housing, a lens, or a personal protection item.

A method for the quantitation of a carboxylic acid end group in a polymer soluble in a halogenated solvent, comprises:
derivatizing a carboxylic acid end group in the polymer with 2-chloro-1,3,2-benzodioxaphosphole to provide a derivatized end group in the presence of a known amount of a reactive standard; and
quantifying the amount of the derivatized end group via $^{31}P$ nuclear magnetic resonance spectroscopy relative to the reactive standard.

The above described and other features are exemplified by the following figures and detailed description.

DETAILED DESCRIPTION

The inventors have discovered a method for the manufacture of poly(aliphatic ester-carbonate)s from dicarboxylic acid and bisphenol monomers in the presence of a carbonyl halide that provides product copolymers having improved hydrostability. In particular, the inventors have unexpectedly found that use of a lower amount of alkali hydroxide in the initial, low-pH stage of the polymerization provides copolymers that have improved hydrolytic stability. In an especially advantageous feature, the method is applicable to large-scale processes and can increase production throughput compared to prior processes.

In another aspect, the method can also provide very high incorporation of the dicarboxylic acid monomer into the copolymers, and thus can provide very low levels of free carboxylic acid (—COOH) end groups in the product copolymer. Without being bound by theory, the inventors have discovered that there is competition between two concurrent reactions, (1) the bisphenol with the carbonyl halide versus (2) the dicarboxylate with the carbonyl halide. The competing reactions can be affected by reaction conditions, and can be controlled in favor of the dicarboxylate/carbonyl halide by adjusting the composition of the reaction mixture in the first, lower pH stage of the reaction. Minimizing the bisphenol/carbonyl halide reaction allows increased dicarboxylate/carbonyl halide reaction to provide the desired haloformate intermediate for ester formation. Increasing the rate or amount of ester formation provides a corresponding decrease in free (—COOH) end groups in the product copolymer. Thus, use of a lower concentration of alkali hydroxide in the first, lower pH stage of the reaction apparently allows near-complete incorporation of the dicarboxylic acid into the copolymer at a pH of 7 to 8. The process and the resulting product provide a two-fold benefit of superior product performance and an increased production throughput compared to use of higher concentrations of alkali hydroxide.

The poly(aliphatic ester-carbonate)s are produced by the reaction of a $C_{6-20}$ aliphatic dicarboxylic acid and a bisphenol as comonomers, which are described in further detail below. The relative amounts of each comonomer are adjusted to provide the desired mole ratio of the $C_{6-20}$ aliphatic dicarboxylic acid units to the bisphenol units in the copolymer. For example, the $C_{6-20}$ aliphatic dicarboxylic acid is present in an amount of 5 to 12 mole percent, or 6 to 10 mole percent, or 7.5 to 10 mole percent, based on the moles of bisphenol.

The process is interfacial, being conducted in a reaction medium comprising water and a water-immiscible organic solvent, for example, methylene dichloride, 1,2-dichloroethane, chlorobenzene, toluene, or the like. In an embodiment the organic solvent is a chlorinated hydrocarbon, typically a chlorinated aliphatic hydrocarbon, preferably methylene dichloride. The ratio of water to organic solvent at the initiation of polymerization can be 1:4 to 4:1 by volume, or 2:3 to 3:2 by volume, for example 4:5 at the beginning of a given batch polymerization.

The polymerization is a two-stage (or higher) process, where the comonomers are treated with a carbonyl dihalide, preferably carbonyl dichloride (phosgene) using a specific pH profile. Thus, an initial polymerization reaction mixture comprising the $C_{6-20}$ dicarboxylic acid, a bisphenol, and an alkali hydroxide, are reacted with an initial portion of a carbonyl dihalide over a first time period, while maintaining the reaction at a first pH from 7.0 to 8.0, or 7.2 to 7.8, or 7.3 to 7.7, preferably 7.4 to 7.6. A second (or final) portion of the carbonyl dihalide is added over a second, subsequent time period while maintaining the reaction pH at a second pH from 9 to 12, preferably from 9.7 to 10.9, to provide a product polymerization mixture comprising the poly(aliphatic ester-carbonate). As is known in the art, the preset pH profile is maintained in the polymerization reaction mixture by addition of dilute alkali hydroxide solution. Vigorous agitation is employed in the polymerization reaction mixture during and after addition of the carbonyl dihalide to ensure homogeneity.

The initial polymerization reaction mixture further contains a strong inorganic base, preferably an alkali hydroxide, more preferably sodium hydroxide or potassium hydroxide. The alkali hydroxide is generally added to the polymerization reaction mixture in the form of an aqueous solution, for example a 10 to 50 wt % aqueous solution (w/w), or a 20 to 40 wt % aqueous solution (w/w).

The alkali hydroxide is present in the initial polymerization reaction mixture to improve the solubility of the comonomers in the reaction medium. Prior art processes generally employ a large quantity of the alkali hydroxide to improve solubility. As described above, however, adjusting the amount of alkali hydroxide to decrease the amount used can positively affect the reaction and allow production of copolymers having improved hydrostability and optionally reduced —COOH end group content. In an embodiment, the amount of alkali hydroxide in the initial polymerization reaction mixture is an amount effective to provide a poly (aliphatic ester-carbonate) having a —COOH end group content of less than 75 parts per million (ppm), preferably less than 50 ppm as measured by $^{31}P$ NMR. In other embodiments, the amount of alkali hydroxide is adjusted to effect an increase in the fraction of the first time period that proceeds at an actual (measured) pH of 7 to 8 compared to the same reaction mixture with a higher amount of alkali hydroxide in the initial polymerization mixture. The fraction of the first time period at a measured pH of 7 to 8 can be at least 70%, preferably at least 80%, more preferably at least 90% of the total duration of the first time period. At the same time, the amount of alkali hydroxide is maintained at a level that allows high throughput, i.e., high production of the copolymer. It has been unexpectedly found that the amount of alkali hydroxide effective to increase the fraction of the first time period that proceeds at an actual (measured) pH of 7 to 8 is of critical importance to achieving the near complete incorporation of dicarboxylic acid into the polymer in the limited time duration available for polymerization and thereby permits achieving high throughput. In an advantageous feature, the methods herein do not increase the second, subsequent period of time compared to the same reaction mixture with a higher amount of alkali hydroxide in the initial polymerization mixture. In other words, use of the methods herein shorten the total time of polymerization, and therefore allow higher throughput in the same amount of time.

The length of the first time period can be more than 9 minutes. In some embodiments, the length of the first time period can be 9 minutes to 30 minutes, or less than 20 minutes, more preferably 11 to less than 20 minutes. The length of the second time period can be 10 minutes or greater, for example 10 to 30 minutes, preferably 13 to 23 minutes. As is known in the art, the increase in pH from the first step to the second step occurs over a finite amount of time, for example 1 to 5 minutes. Herein, the time spent during the pH increase from first low pH step to second high pH step is included within the second time period.

The initial portion of the carbonyl dihalide add during the first time period can be 28 to 50% of the total amount of carbonyl dihalide, preferably 32 to 43% of the total amount of carbonyl dihalide. The second portion of the carbonyl dihalide can be the remaining amount to provide addition of 100% of the desired amount of carbonyl halide.

The polymerization can further be conducted in the presence of a catalyst system. Catalyst systems are known in the art, and include, for example, various tertiary amines as condensation catalysts and phase transfer catalysts. Among tertiary amines that can be used as catalysts in interfacial polymerization are aliphatic tertiary amines such as triethylamine and tributylamine, cycloaliphatic tertiary amines such as N,N-diethyl-cyclohexylamine, and aromatic tertiary amines such as N,N-dimethylaniline. Phase transfer catalysts that can be used are catalysts of the formula $(R^3)_4Q^+X$, wherein each $R^3$ is the same or different, and is a $C_{1-10}$ alkyl; Q is a nitrogen or phosphorus atom; and X is a halogen atom or a $C_{1-8}$ alkoxy or $C_{6-18}$ aryloxy. Exemplary phase transfer catalysts include $(CH_3(CH_2)_3)_4NX$, $(CH_3(CH_2)_3)_4PX$, $(CH_3(CH_2)_5)_4NX$, $(CH_3(CH_2)_6)_4NX$, $(CH_3(CH_2)_4NX$, $CH_3(CH_3(CH_2)_3)_3NX$, and $CH_3(CH_3(CH_2)_2)_3NX$, wherein X is Cl$^-$, Br$^-$, a $C_{1-8}$ alkoxy or a $C_{6-18}$ aryloxy. In an embodiment, the catalyst system comprises triethyl amine and methyltributyl ammonium halide or hexabutylbutylene diammonium halide. An effective amount of the catalyst system can be 0.1 to 10 wt %, or 0.5 to 2 wt %, each based on the weight of bisphenol in the reaction mixture. Alternatively, the amount of tertiary amine catalyst can be expressed as 0.75 to 3.0 mole percent, based on the moles of bisphenol.

Other components as is known in the art can be present in the polymerization reaction mixture. For example, an endcapping agent (also referred to as a chain stopper or chain terminating agent) can be included during polymerization to provide end groups. Exemplary endcapping agents include monocyclic phenols such as phenol and $C_1$-$C_{22}$ alkyl-substituted phenols such as p-cumylphenol (PCP), resorcinol monobenzoate, and p- and tertiary-butyl phenol, monoethers of diphenols, such as p-methoxyphenol, and alkyl-substituted phenols with branched chain alkyl substituents having 8 to 9 carbon atoms, 4-substituted-2-hydroxybenzophenones and their derivatives, aryl salicylates, monoesters of diphenols such as resorcinol monobenzoate, mono-carboxylic acid chlorides such as benzoyl chloride, $C_1$-$C_{22}$ alkyl-substituted benzoyl chloride, toluoyl chloride, bromobenzoyl chloride, cinnamoyl chloride, and 4-nadimidobenzoyl chloride, polycyclic, mono-carboxylic acid chlorides such as trimellitic anhydride chloride, and naphthoyl chloride, functionalized chlorides of aliphatic monocarboxylic acids, such as acryloyl chloride and methacryoyl chloride, and monochloroformates such as phenyl chloroformate, alkyl-substituted phenyl chloroformates, p-cumyl phenyl chloroformate, and toluene chloroformate. Combinations of different end groups can be used. The amount of endcapping agent in the polymerization reaction mixture is adjusted to provide the desired copolymer molecular weight, as is known in the art. For example, the amount of endcapping agent can be 0.1 to 10 mol %, based on the amount of bisphenol.

A chelating agent can be present to remove residuals from (for example) the components in the operations systems. To remove this iron, sodium gluconate can be added as a chelating agent in an effective amount, which can be determined by one of ordinary skill in the art without undue experimentation. Exemplary amounts can be 1 to 1,000 parts per million by weight, based on the amount of water used.

The order of addition of the reactants and other components present during polymerization can be varied. As used herein, the term "initial polymerization reaction mixture" is a term of convenience referring to all components present during the polymerization except for the carbonyl dihalide. Thus, in some embodiments, all of the components used in the polymerization are pre-combined, and thus present simultaneously before the carbonyl dihalide is added to initiate polymerization. In other embodiments, not all of the components are pre-combined; instead, some of the components are pre-combined, and the remaining components are added with or after the carbonyl dihalide. In these embodiments, "providing the initial polymerization reaction mixture" occurs simultaneously with addition of the carbonyl dihalide. These various embodiments are described in more detail below.

For example, the bisphenol, water, organic solvent, $C_{6-20}$ aliphatic dicarboxylic acid, optionally the catalyst system, and optionally all or a portion of the alkali metal hydroxide can be combined in a preformulation tank, and then transferred to a batch polymerization reactor. Where all of the alkali metal hydroxide is added in the preformulation tank, polymerization is initiated by the addition of the carbonyl dihalide. Alternatively, where none or only a portion of the alkali metal hydroxide is added in the preformulation tank, any remaining portion of the alkali metal hydroxide can be added to the batch polymerization reactor before or after transfer, and then the polymerization initiated by the addition of the carbonyl dihalide.

In a specific example of this embodiment, the $C_{6-2}$ aliphatic dicarboxylic acid, and the bisphenol A are added as powder to the formulation tank, together with 33 wt % alkali hydroxide solution, in a stoichiometric equivalence of two moles dry caustic per mole of dicarboxylic acid, along with solvent, water, chelating agent and catalyst. Generally, a 10% excess caustic can be used on dry caustic moles basis, based on the moles of the dicarboxylic acid. The mixture is stirred for up to 30 mins to form a slurry in the formulation tank. The slurry from formulation tank is transferred to the reactor and is then phosgenated. A 33 wt % alkali hydroxide solution is added as needed to maintain the desired pH profile. The phosgene set point for the polymerization is selected to allow for batch completion in a robust fashion and is 15 to 50% in excess of stoichiometric requirement. An endcapping agent can be added to the reactor before or after polymerization is initiated. For the first part of the reaction that typically starts at the beginning of phosgenation and ends at less than or equal to 50% of batch phosgene set point, the pH is maintained in the range of 7 to 8. The pH set point is then ramped from 7.5 to 10.3 for the remainder of the batch phosgene addition duration to complete polycarbonate formation and hence complete the polymerization of the reaction materials.

In another specific example of this embodiment, the dicarboxylic acid is added in powder form to the formulation tank along with bisphenol, solvent, water, chelating agent, and catalyst. The polymerization reactor is charged alkali hydroxide solution (e.g., 33 wt %) in stoichiometric equivalence of two moles dry caustic per mole of dicarboxylic acid. Additionally, a 10% excess caustic can be used on dry caustic basis. The slurry from the formulation tank is transferred to the reactor and is then phosgenated while maintaining the desired pH profile with addition of alkali hydroxide solution (e.g., 33 wt %). The phosgene set point for the batch is chosen to allow for batch completion in a robust fashion and is 15 to 50% in excess of stoichiometric quantity. For the first part of the reaction, which typically starts at the start of phosgene addition and ends at up to 50% of batch phosgene set point. pH is maintained in the range of 7 to 8. The batch pH set point is then gradually increased to 10.3 for the remainder of the batch to complete polycarbonate formation.

In a second embodiment, the bisphenol, water, organic solvent, and optionally the catalyst system are first combined in a formulation tank, followed by the addition of the $C_{6-20}$ aliphatic dicarboxylic acid. The $C_{6-20}$ aliphatic dicarboxylic acid can be added to the process by various delivery modes. For example, the $C_{6-20}$ aliphatic dicarboxylic acid can be added as a solid or as a slurry in water, and the alkali metal hydroxide can be added separately. Alternatively, the $C_{6-20}$ aliphatic dicarboxylic acid can be pre-dissolved in water by the addition of the alkali metal hydroxide. Additional alkali metal hydroxide, generally in the form of an aqueous solution, can be added to the formulation tank to further help dissolve the bisphenol and the $C_{6-20}$ aliphatic dicarboxylic acid. The mixture can be stirred to form a slurry and transferred to a polymerization reactor. Optionally, the formulation tank can be rinsed with the solvent to ensure complete slurry transfer to the reactor. Polymerization is initiated by the addition of the carbonyl dihalide to the polymerization reactor. The endcapping agent can be added to the reactor before or after polymerization is initiated.

In a third embodiment of the process, the bisphenol, water, and organic solvent are pre-combined, and then transferred to a polymerization reactor, and the $C_{6-20}$ aliphatic dicarboxylic acid is added to the polymerization reactor. Again, the $C_{6-20}$ aliphatic dicarboxylic acid can be added as a solid, or as a slurry in water separately from the alkali metal hydroxide; or the $C_{6-20}$ aliphatic dicarboxylic acid can be added to the reactor as a solution pre-dissolved in water by the addition of the alkali metal hydroxide. In this embodiment, the direct addition of the $C_{6-20}$ aliphatic dicarboxylic acid to the polymerization reactor can occur before or during addition of the carbonyl dihalide, for example during the phosgenation step. The endcapping agent can be added to the reactor before or after polymerization is initiated. Similarly, the catalyst system can be added to the reaction mixture either before the carbonyl dihalide or at a suitable stage during reaction. Preferably the catalyst system is charged to the reaction mixture before addition of the carbonyl dihalide.

In a specific example of this third embodiment, the $C_{6-20}$ aliphatic dicarboxylic acid is pre-dissolved in water by addition of the base in an amount effective to provide a stoichiometric equivalence with the —COOH functional group moieties. Generally, a 10% excess caustic can be used on molar basis. The dicarboxylic acid solution is added to the other components of the polymerization mixture at the beginning of reaction after all of the other components, including catalyst, have been charged to the reactor. The carbonyl dihalide set point is selected to achieve substantial completion of the reaction, which is generally a 15 to 50% excess of stoichiometric quantity. For up to 50% of the total carbonyl dihalide added during the polymerization reaction, the pH of the reaction is maintained in the range of 7 to 8 with a target pH of 7.5. After the addition of the dicarboxylic acid solution is complete, the pH set point is increased from 7.5 to 10.3 over 3.5 minutes and is held at 10.3 during the remainder of the carbonyl dihalide addition.

The poly(aliphatic ester-carbonates) produced by the processes described herein are copolymers that include aliphatic ester units and aromatic carbonate units of formula (1)

(1)

wherein R is an aliphatic $C_{4-20}$, or $C_{6-16}$, or $C_{10-12}$ group derived from a dicarboxylic acid (2) as described below, and each $R^1$ is independently derived from a dihydroxyaromatic compound of formula (3) as described below, and x and y each represent average weight percentages of the aliphatic ester units and the carbonate units, wherein the average ratio of x:y is 10:90 to 0.5:99.5, specifically 9:91 to 1:99, and more specifically 8:92 to 3:97, where x+y is 100

In some embodiments, the poly(aliphatic ester-carbonates) produced by the processes described herein are copolymers that include aliphatic ester units and aromatic carbonate units of formula (1a)

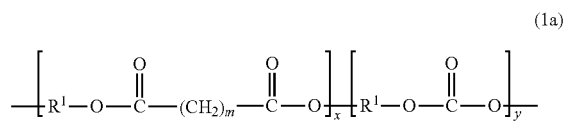
(1a)

where each $R^1$ is independently derived from a bisphenol of formula (2) as described below, m is 6 to 20, and x and y each represent average weight percentages of the aliphatic ester units and the carbonate units, wherein the average ratio of x:y is 10:90 to 0.5:99.5, specifically 9:91 to 1:99, and more specifically 8:92 to 3:97, where x+y is 100.

The aliphatic ester units are derived from a $C_{6-20}$, or a $C_{6-18}$, or a $C_{10-12}$ aliphatic dicarboxylic acid, or reactive derivative thereof. As used herein, an "aliphatic" carboxylic acid is not aromatic, and can include cyclic or noncyclic, straight or branched chain groups, and can be fully saturated, or contain up to three unsaturations. In an embodiment, the aliphatic dicarboxylic acid is cyclic or straight chain, and is fully saturated. The carboxylic acid groups of the noncyclic dicarboxylic acids can be substituted at the terminal ends or along the backbone, and are preferably alpha, omega dicarboxylic acids substituted at each terminal end. Exemplary dicarboxylic acids include $C_{10-12}$ aliphatic di carboxylic acids such as cyclohexane dioic acid, hexanedioic acid (also referred to as adipic acid); $C_{10}$ dicarboxylic acids such as decanedioic acid (also referred to as sebacic acid, or SBA); and $C_{12}$ dicarboxylic acids such as dodecanedioic acid (sometimes abbreviated as DDDA). It will be appreciated that the aliphatic dicarboxylic acid is not limited to these exemplary carbon chain lengths, and that other chain lengths within the $C_{6-20}$ limitation can be used.

The aliphatic ester units and the carbonate units are further derived from a bisphenol of formula (2)

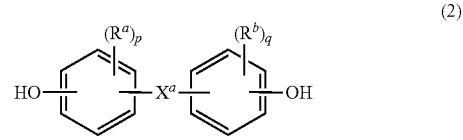
(2)

wherein $R^a$ and $R^b$ are each independently a halogen, $C_{1-12}$ alkoxy, or $C_{1-12}$ alkyl, and p and q are each independently integers of 0 to 4, such that when p or q is less than 4, the valence of each carbon of the ring is filled by hydrogen. In an embodiment, p and q is each 0, or p and q is each 1 and $R^a$ and $R^b$ are each a $C_{1-3}$ alkyl group, specifically methyl, disposed meta to the hydroxy group on each arylene group. Further in formula (2), $X^a$ is a bridging group connecting the two hydroxy-substituted aromatic groups, where the bridging group and the hydroxy substituent of each $C_6$ arylene group are disposed ortho, meta, or para (preferably para) to each other on the $C_6$ arylene group, for example, a single bond, —O—, —S—, —S(O)—, —S(O)$_2$—, —C(O)—, or a $C_{1-18}$ organic group, which can be cyclic or acyclic, aromatic or non-aromatic, and can further comprise heteroatoms such as halogens, oxygen, nitrogen, sulfur, silicon, or phosphorous. For example, $X^a$ can be a substituted or unsubstituted $C_{3-18}$ cycloalkylidene; a $C_{1-25}$ alkylidene of the formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl; or a group of the formula —C(=$R^e$)— wherein $R^e$ is a divalent $C_{1-12}$ hydrocarbon group.

Some illustrative examples of bisphenol compounds that can be used are described, for example, in WO 2013/175448 A1, US 2014/0295363, and WO 2014/072923. Specific dihydroxy compounds include 4,4'-dihydroxybiphenyl, 2,2-bis(4-hydroxyphenyl) propane ("bisphenol A" or "BPA"), 1,6-dihydroxynaphthalene, 2,6-dihydroxynaphthalene, bis (4-hydroxyphenyl)methane, bis(4-hydroxyphenyl)diphenylmethane, bis(4-hydroxyphenyl)-1-naphthylmethane, 1,2-bis (4-hydroxyphenyl)ethane, 1,1-bis(4-hydroxyphenyl)-1-phenylethane, 2-(4-hydroxyphenyl)-2-(3-hydroxyphenyl) propane, 1,1-bis(4-hydroxy-3-methylphenyl)cyclohexane, and 1,1-bis(4-hydroxyphenyl)-3,3,5-trimethylcyclohexane ("TMC").

In some embodiments, the poly(aliphatic ester-carbonate) is derived from bisphenol A, as shown in formula (1a)

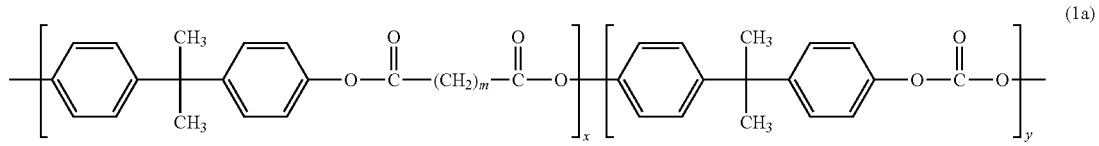
(1a)

where m is 6 to 20, preferably 8 to 10, and x and y are as defined for formula (1). In an embodiment, the poly(aliphatic ester-carbonate) comprises sebacic acid ester units and bisphenol A carbonate units (formula (1a), where m is 8), and the average mole ratio of x:y is 8:92 to 3:97, or 7:93 to 5:95.

The poly(aliphatic ester-carbonate)s manufactured by this method can have a weight average molecular weight (Mw) of 10,000 to 50,000 Dalton (Da), or 20,000 to 38,000 Da (measured by gel permeation chromatography (GPC) using a polystyrene standard, corrected for polycarbonate). In a preferred embodiment, the copolymer has an Mw of 35,500 to 37,500 Da. In another preferred embodiment, the Mw is 20,000 to 25.000 Da.

The poly(aliphatic ester-carbonate)s preferably comprise 5 to 12 mol %, or 6 to 10 mol %, or 7.5 to 9 mol % of units derived from the $C_{6-20}$ aliphatic dicarboxylic acid, as measured by proton nuclear magnetic resonance ($^1$H NMR) spectroscopy or by near infrared (NIR) spectroscopy.

The poly(aliphatic ester-carbonate)s have improved hydrolytic stability, compared to poly(aliphatic ester-carbonate)s manufactured by the same process, but with a shorter time spent a the lower pH. For example, the poly (aliphatic ester-carbonate)s can have a decrease in weight average molecular weight of less than 30%, preferably less than 20% after heat aging a molded sample for 4 weeks at 85° C. and 85% humidity; or a decrease in weight average molecular weight of less than 60%, preferably less than 50% after heat aging a molded sample for 8 weeks at 85° C. and 85% humidity.

In another embodiment, the poly(aliphatic ester-carbonate) can have a —COOH end group content of less than 75 parts per million, preferably less than 50 parts per million, as measured, for example, by $^{31}$P nuclear magnetic resonance (NMR) spectroscopy.

The poly(aliphatic ester-carbonate)s can further have other advantageous properties. For example, the poly(aliphatic ester-carbonate)s can have excellent clarity and light transmission properties. For example, the poly(aliphatic ester-carbonate) can have 80 to 100% transmission, more specifically, 89 to 100% light transmission as determined by ASTM D1003-11, using 3.2 mm thick plaques. The poly (aliphatic ester-carbonate) can also have low haze, specifically 0.001 to 5%, more specifically, 0.001 to 1% as determined by ASTM D1003-11 using 3.2 mm thick plaques.

The poly(aliphatic ester-carbonate)s can have excellent flow properties, for example a melt volume flow rate (MVR) of 13 cc/10 min or higher at 250° C. and 1.2 kg load, for example 13 to 25 cc/10 min or higher at 250° C. and 1.2 kg load.

The poly(aliphatic ester-carbonate)s can have a glass transition temperature of 110 to 145° C., or of 115 to 145° C. or of 128 to 139° C. or of 130 to 139° C.

The poly(aliphatic ester-carbonate)s can be used in polymer compositions for the formation of articles. The polymer composition can further include one or more additives. The one or more additives can be selected to achieve a desired property, with the proviso that the additives are also selected so as to not significantly adversely affect a desired property of the polymer composition. The additive composition or individual additives can be mixed at a suitable time during the mixing of the components for forming the polymer composition. The one or more additives can include a particulate filler, antioxidant, heat stabilizer, light stabilizer, ultraviolet light stabilizer, UV absorbing additive, plasticizer, lubricant, release agent, antistatic agent, anti-fog agent, antimicrobial agent, colorant, surface effect additive, radiation stabilizer, flame retardant, anti-drip agent, or a combination comprising at least one of the foregoing. The additives are used in the amounts generally known to be effective. For example, the total amount of the additives (other than any impact modifier, filler, or reinforcing agent) can be 0.001 to 10.0 wt %, or 0.01 to 5 wt %, each based on the total weight of the polymer components in the polymer composition. In an embodiment, the polymer composition further comprises an impact modifier, filler, reinforcing agent, anti-oxidant, thermal stabilizer, light stabilizer, ultraviolet light absorber, quencher, plasticizer, lubricant, mold release agents anti-static agent, colorant, blowing agent, flame retardant, anti-drip agent, radiation stabilizer, or a combination comprising at least one of the foregoing. In some embodiments, the polymer composition is devoid of any additives not intentionally added to the polymer composition.

The polymer composition can be prepared according to any method that is generally known. In some embodiments, the polymer composition is prepared by melt-mixing or a combination of dry-blending and melt-mixing. Melt-mixing can be performed in single or twin screw type extruders or similar mixing devices which can apply a shear and heat to the components. Melt-mixing can be performed at temperatures greater than or equal to the melting temperatures of the polymer components and less than the degradation temperatures of either of the polymer components. All of the ingredients can be added initially to the processing system. In some embodiments, the ingredients can be added sequentially or through the use of one or more master batches. It can be advantageous to apply a vacuum to the melt through one or more vent ports in the extruder to remove volatile impurities in the composition. In some embodiments the composition is the product of melt-mixing the polymers and, when present, any additives.

The poly(aliphatic ester-carbonate)s and polymer compositions are useful in a wide variety of applications, especially applications where improved stability under hot, humid conditions is desired. Articles of this type include medical articles, food preparation, storage, and consumption articles, housings, and lenses, including automotive lenses, corrective lenses and safety eyewear, as well as other personal protection items such as face shields or personal protection equipment for sports. In some embodiments the articles are thin articles, where it can be particularly difficult to obtain hydrostability. Thin articles include those that include a portion having a thickness in in the range of 0.5 mm to 2 cm, or of 0.1 mm to 10 mm.

The articles can be manufactured by any process, such as extruding, casting, and the like, but molding is especially useful, such as such as injection molding, compression molding, thermoforming, or blow molding. Injection molding is preferred in some embodiments, especially for thin articles.

Further disclosed herein is a method for quantifying a carboxylic acid end group in a polymer soluble in a halogenated solvent. The method comprises selective derivatization of the —COOH end group with a reactive phosphorus containing agent (e.g., 2-chloro-1,3,2-benzodioxaphosphole), then quantifying the derivatized end groups using $^{31}$P NMR. Quantification is most readily carried out by conducting the derivatization in the presence of a known amount of a reactive standard, for example mesitol or 2,4,6-trichlorophenol. Detection limits are currently in the 3 to 5 ppm range, with quantification limits in the 10 to 15 ppm range.

This disclosure is further illustrated by the following examples, which are non-limiting.

EXAMPLES

The following procedures were used in the Examples.

Determination of hydroxyl or carboxyl groups in polycarbonate polymers: This method applies to polymers that are soluble in chloroform or 1,1,2,2-tetrachloroethane, where free endcapped structures have a reactive functional group such as hydroxyl (—OH) or —COOH groups. Typical sample weights are 200 to 250 mg and in some cases where end groups are extremely low, as much as 400 to 500 mg of sample can be used. The sample is first derivatized using 2-chloro-1,3,2-benzodioxaphosphole and analyzed using $^{31}$P NMR. Quantification is accomplished by integrating the derivatized end groups against a standard (mesitol or 2,4,6-trichlorophenol (TCP)).

More specifically, the sample is prepared by preparing a 0.5 M solution of chromium(III) acetylacetonate. An internal standard is prepared by adding a known amount of mesitol or trichlorophenol into a tared volumetric flask, adding sufficient of pyridine to dissolve, then filling to volume with the solution of chloroform and chromium(III) acetylacetonate. The sample to be analyzed is placed in a vial and a known amount of the internal standard solution is added, followed by 2-chloro-1,3,2-benzodioxaphosphole (warmed, if solid). The contents of the sample are immediately transferred to an NMR tube and a $^{31}$P NMR spectrum is immediately acquired. Acquired time domain data are Fourier transformed. A line broadening factor of 3 Hz with exponential apodization is applied before Fourier transformation. Manual phase correction and a multi-point baseline correction are applied. Care is taken to produce a nearly perfectly phased spectrum to obtain a flat baseline.

The mesitol peak (132.12 ppm) or TCP peak (131.09 ppm) are used to determine the chemical shift of the appropriate end group, and are set to a predetermined integral value, allowing quantitation of the —COOH by known methods. The PPC-derivatized $^{31}$P chemical shift (ppm relative to mesitol at 132.12 ppm or TCP at 131.09 ppm) for sebacic acid —COOH is 129.43 ppm.

Molecular Weight Drop Measurement: A measure of quality of PEC copolymers is the drop in molecular weight when subjected to a diisobutylamine (DIBA) test, the "Mw drop test." In the Mw drop test, a polymer sample dissolved in a solvent suitable for GPC is added to two small vials. A strong acid such as 1 to 2 N HCl is added to one vial in an amount equal to the copolymer solution, and DIBA is added to the second vial. After standing both vials for 5 mins, the vial containing DIBA is quenched with HCl. The copolymer phases in each of the vials are separated, purified with distilled, deionized (DI) water, and Mw is measured. Mw drop is then calculated as the percentage reduction in Mw of polymer in the vial with DIBA compared to Mw of polymer in the vial with HCl. A molecular weight drop of less than 10% is considered acceptable.

Determination of Hydrostability: To determine hydrostability, copolymer from a control sample and an experimental sample were each mixed with a stabilizer package and molded into 0.125-inch color chips. Immediately after molding, the samples were measured for Mw of the polymer via GPC. Then, the color chips were placed in the hydrolytic oven, where the samples were hydrolytically aged at 85% humidity and 85° C. ("hydroaging"). Samples were withdrawn after 4 weeks and 8 weeks each, and Mw was measured.

Example 1

This example describes a process wherein, in contrast to prior art processes, the amount of caustic (e.g., alkali hydroxide) is decreased, to decrease the amount of pre-equilibration time. In a process for the preparation of a high flow PEC derived from SBA and bisphenol A, a reactant mixture was formulated by combining BPA, water, dichloromethane, trimethylamine catalyst, sodium gluconate, and PCP in dichloromethane. This mixture was charged to a batch polymerization stirred tank reactor. Separately, a 10 wt % solution of SBA in NaOH was prepared by dissolution of SBA powder in 33 wt % NaOH, followed by addition of DI water. This solution was then fed to the reactor to provide a concentration of 7.5 to 9.0 mol % of SBA in the final polymer. Next, phosgene addition was started. The pH in the reactor was maintained at a target of 7.5 by addition of 33 wt % aqueous NaOH until 47% of the total phosgene calculated to be required for completion of the reaction was added. The batch total phosgene set point was calculated at 48% excess over the stoichiometric phosgene required for the batch bisphenol A charge. The pH was then ramped up to 10.3 for the remainder of the phosgene addition while maintaining the phosgene addition rate. The phosgene addition rate was then dropped in three steps as polymerization progressed. The final 10 to 15% of the phosgene addition was then carried out.

Six polymer batches produced by this reaction process yielded a high flow PEC copolymer with an average Mw of 35.346 Da, containing 8.41 to 8.65 mol % SBA. The residual SBA in brine was very low, i.e., below the detectable limit of <21.4 ppm as measured by ultra-performance liquid chromatography (UPLC) coupled with an Evaporative Light Scattering Detector. The molecular weight drop for the copolymer made using this technique was found to be 4.32%. The batch reaction process described in this example illustrates a successful method for preparation of a copolymer of SBA and BPA containing acceptably low residual SBA in reaction brine upon completion of the batch. This process yielded copolymer powders with unreacted —COOH end groups of 99 ppm on average, with the range of 75 to 156 ppm. These levels are lower than the same reaction conducted using a higher amount of caustic in the first step of the polymerization.

Comparative Example 2

This example can be executed on either the pilot plant or manufacturing plant scale, e.g., on a scale of 200 to 9,000 pounds (90.7 to 4082 kilogram). Accordingly, a formulation tank is charged with SBA, BPA, 33 wt % sodium hydroxide solution, water, dichloromethane, triethylamine, and sodium gluconate. The amount of SBA in the reaction mixture was 0.094 moles per mole of BPA, the amount of catalyst was 0.017 moles per mole of BPA, the amount of NaOH was 0.223 moles per mole of BPA, and the amount of sodium gluconate was 0.33 lbs for every 1000 lbs of water in the formulation. The contents of the formulation tank were transferred to a batch polymerization stirred tank reactor. Then, an additional amount of 33 wt % NaOH solution (w/v) was added to the reactor before phosgene addition was started, to dissolve more of the comonomers. The amount of NaOH added was 0.213 moles of NaOH per mole of BPA. After receiving all reactants, phosgene addition to the reactor was started. PCP endcapping agent was delivered to the reactor as a solution in dichloromethane. The pH in the reactor was maintained at 7.5 target by addition of 33% aqueous NaOH (w/v) until 40% of the total phosgene calculated to be required for completion was added. The batch total phosgene set point was calculated with 48% excess over the stoichiometric phosgene required for complete polymerization of the batch bisphenol A charge. The pH was then ramped up to 10.3 for rest of the addition.

Thirty-two polymer batches produced by this reaction process yielded a high flow PEC copolymer with an average Mw of 35.950 Da, and containing 8.03 to 8.13 mol % SBA. The residual SBA in brine was consistently at below a detectable limit of <21.4 ppm as measured by a UPLC coupled with an Evaporative Light Scattering Detector. Mw drop was found to be between 0 and 5.3%. The batch reaction process described in this example illustrates another method for successful preparation of a copolycarbonate of SBA and BPA containing acceptably low residual SBA in reaction brine upon completion of the batch. Hydrostability was determined as described above.

Inventive Example 1

In this example, a formulation tank was charged with SBA, BPA, 33 wt % sodium hydroxide solution, water, dichloromethane, triethylamine, and sodium gluconate. The amount of SBA in the reaction mixture was 0.094 moles per mole of BPA, the amount of catalyst was 0.17 moles per mole of BPA, the amount of NaOH was 0.223 moles per mole of BPA, and the amount of sodium gluconate was 0.33 lbs for every 1000 lbs of water in the formulation. The contents of the formulation tank were transferred to a batch polymerization stirred tank reactor. After receiving all reactants, phosgene addition was started to the reactor with no additional 33 wt % NaOH added. PCP endcapping agent was delivered to the reactor as a solution in dichloromethane. The pH in the reactor was maintained at 7.5 by addition of 33% aqueous NaOH until 39% of the total phosgene calculated to be required to complete the reaction was added. The batch total phosgene set point was calculated with 48% excess over the stoichiometric phosgene required for complete polymerization of the batch bisphenol A charge. The pH was then ramped up to 10.3 for rest of the addition. The pH was then ramped up to 10.3 and maintained for rest of the phosgene addition.

Twenty-five polymer batches produced by this reaction process yielded a high flow PEC copolymer with an average Mw of 36,106 Da containing 8.14 mol % SBA. The residual SBA in brine was consistently at below a detectable limit of less than 21.4 ppm as measured by a UPLC coupled with an Evaporative Light Scattering Detector. Mw drop was found to be 0-3.5%. The batch reaction process described in this example illustrates a successful method for preparation of a copolymer of SBA and BPA containing acceptably low residual SBA in reaction brine upon completion of the batch. Hydrostability was determined as described above.

Thus, this process does not use the second addition of caustic in the first step just prior to phosgene addition as used in the process in Example 2 above. Also, it uses 39% of total phosgene in the step 1 at pH of 7.5 unlike examples 1 and 2 which use higher. Both of these conditions lead to a different reaction composition from the start of the 7.5 pH step which results in improved hydrostability as shown below.

Hydrostability Testing Results

The table shows the results of hydrostability testing on five different samples. Three trials (A, B, and C) were carried out at the reaction process conditions of Example 3. The Table further shows the results of two trials (D and E) carried out at the reaction process conditions of Comparative Example 2.

| Trial | Unreacted —COOH end groups in copolymer before hydroaging (ppm) | | Percent drop in Mw after hydroaging | |
|---|---|---|---|---|
| | Average | Range | 4 weeks | 8 weeks |
| A | 53.8 | 33-67 | 18% | 39% |
| B | 23.0 | 20-26 | 21% | 43% |
| C | 31.0 | 5-50 | 19% | 46% |
| D* | 237.5 | 204-258 | 36% | 65% |
| E* | 295.5 | 295.5 | 46% | 79% |

*Comparative

The percent drop in Mw measured in these tests shows that for the copolymers made by the method of Example 3 (Trials A, B, and C), the Mw does not decrease by more than 50% of its initial Mw even after subjecting it to harsh conditions of elevated humidity and temperature. Thus, the copolymers made by the process used for trials A. B, and C possesses very good hydrolytic stability.

The Table further shows the substantially higher level of Mw loss in the copolymers of Trials D and E during hydrostability testing when higher amounts of caustic were used in the polymerization, where the Mw of the polymer degrades as much 80% of the initial Mw.

Inventive Example 4

Another high flow PEC derived from SBA and bisphenol A was prepared in accordance with the procedure in Example 3, except that the pH in the reactor was maintained at 7.5 by addition of 33 wt % aqueous NaOH until 35% of the total phosgene calculated to be required to complete the reaction was added. The target Mw range was 20.900-21,900 Da. and the copolymer contained 5.5 to 6.5 mol % SBA.

This disclosure further encompasses the following embodiments.

Embodiment 1

An interfacial process for preparing a poly(aliphatic ester-carbonate), the process comprising providing an initial polymerization reaction mixture comprising an aliphatic $C_{6-20}$ dicarboxylic acid, a bisphenol, an alkali hydroxide, and optionally a catalyst, in a solvent system comprising water and an immiscible organic solvent, adding an initial portion of a carbonyl dihalide over a first time period while maintaining the reaction at a first pH from 7 to 8; and adding a second portion of the carbonyl dihalide over a second, subsequent time period while maintaining the reaction pH at a second pH from 9 to 12, to provide a product polymerization mixture comprising the poly(aliphatic ester-carbonate).

wherein the amount of alkali hydroxide in the initial polymerization reaction mixture is an amount effective to increase the fraction of the first time period at a measured pH of 7 to 8 compared to the same reaction mixture with a higher amount of alkali hydroxide in the initial polymerization mixture.

Embodiment 2

The Embodiment of claim 1, wherein no additional alkali hydroxide is added after adding the providing the initial polymerization reaction mixture and before adding the initial portion of the carbonyl dihalide, or after the adding the initial portion of the carbonyl dihalide.

Embodiment 3

The process of one or more of the preceding Embodiments, wherein the fraction of the first time period at a measured pH of 7 to 8 is at least 70%, preferably at least 80%, more preferably at least 90% of the total duration of the first time period.

Embodiment 4

The process of one or more of the preceding Embodiments, wherein the amount of alkali hydroxide in the initial polymerization reaction mixture is an amount effective to provide a poly(aliphatic ester-carbonate) having a —COOH end group content of less than 75 parts per million, preferably less than 50 parts per million as measured by $^{31}$P NMR.

Embodiment 5

The process of any one or more of the preceding Embodiments, wherein
the length of the first time period is more than 9 minutes, for example 9 to 30 minutes; greater than 9 to 30 minutes, preferably 10 to 20 minutes; and
the length of the second time period is 10 minutes or greater, for example from 10 to 30 minutes, preferably 13 to 23 minutes.

Embodiment 6

The process of any one or more of the preceding Embodiments, wherein
the first pH is from 7.0 to 8.0, preferably 7.3 to 7.7; and
the second pH is from 9.7 to 10.9.

Embodiment 7

The process of any one or more of the preceding Embodiments, wherein
the initial portion of the carbonyl dihalide is 28 to 50% of the total amount of carbonyl dihalide, preferably 32 to 43% of the total amount of carbonyl dihalide used in the process.

Embodiment 8

The process of any one or more of the preceding Embodiments, wherein the providing the initial reaction mixture comprises combining the $C_{6-20}$ aliphatic dicarboxylic acid, bisphenol, water, alkali metal hydroxide, organic solvent, and optionally the catalyst system before adding the carbonyl dihalide.

Embodiment 9

The process of Embodiment 8, comprising pre-combining the $C_{6-20}$ aliphatic dicarboxylic acid, bisphenol, water, organic solvent, and optionally the catalyst system; and then adding the alkali metal hydroxide before adding the carbonyl dihalide.

Embodiment 10

The process of any one or more of Embodiments 1 to 7, wherein the providing the initial polymerization reaction mixture comprises pre-combining the bisphenol, water, organic solvent, and optionally the catalyst system; then adding the $C_{6-20}$ aliphatic dicarboxylic acid and the alkali hydroxide solution before adding the carbonyl dihalide.

Embodiment 11

The process of any one or more of Embodiments 1 to 7, wherein the forming the initial polymerization reaction mixture comprises combining the bisphenol, water, organic solvent, and optionally the catalyst system; then adding the $C_{6-20}$ aliphatic dicarboxylic acid with the addition of the carbonyl dihalide.

Embodiment 12

The process of Embodiment 10 or Embodiment 11, wherein
the $C_{6-20}$ aliphatic dicarboxylic acid is added as a solid or as a slurry separately from the alkali hydroxide solution; or
the $C_{6-20}$ aliphatic dicarboxylic acid is pre-dissolved in water with the alkali hydroxide, then added.

Embodiment 13

The process of any one or more of the preceding Embodiments, wherein
the aliphatic $C_{6-20}$ dicarboxylic acid is azelaic acid, sebacic acid, or dodecanedioic acid, preferably sebacic acid;
the bisphenol is bisphenol A;
the alkali hydroxide is sodium hydroxide; and
the carbonyl dihalide is carbonyl dichloride.

Embodiment 14

The process of any one or more of the preceding Embodiments, wherein
the aliphatic $C_{6-20}$ dicarboxylic acid is present in an amount of 5 to 12 mole percent, or 6 to 10 mole percent, or 7.5 to 9 mole percent, based on the moles of bisphenol.

Embodiment 15

The process of any one or more of the preceding Embodiments, wherein the catalyst is a tertiary amine catalyst, and is present in an amount of 0.75 to 3.0 mole percent, based on the moles of bisphenol.

Embodiment 16

A poly(aliphatic ester-carbonate) made by the method of any one or more of the preceding Embodiments.

Embodiment 17

The poly(aliphatic ester-carbonate) of Embodiment 16, having
a weight average molecular weight of 10,000 to 50,000 Dalton, or 20,000 to 38,000 Dalton, or 20,000 to 25,000 Dalton, measured by gel permeation chromatography, based on bisphenol A polycarbonate standards);
5 to 12 mol %, or 6 to 10 mol %, or 7.5 to 9 mol % of units derived from the $C_{6-20}$ aliphatic dicarboxylic acid;
a glass transition temperature of 110 to 145° C. or 115 to 145° C., or 128 to 139° C., or 130 to 139° C.;
a decrease in weight average molecular weight of less than 30%, preferably less than 20% after heat aging a molded sample for 4 weeks at 85° C. and 85% humidity; a decrease in weight average molecular weight of less than 60%, preferably less than 50% after heat aging a molded sample for 8 weeks at 85° C. and 85% humidity; and a —COOH end group content of less than 75 parts per million, preferably less than 50 parts per million as measured by $^{31}$P NMR Embodiment 18

A polymer composition comprising the poly(aliphatic ester-carbonate) of Embodiment 16 or Embodiment 17, and further comprising an additive.

Embodiment 19

An article subject to conditions of heat and humidity comprising the poly(aliphatic ester-carbonate) composition of Embodiment 16, preferably a medical article, a food preparation, storage, or consumption article, a housing, an automotive article, a lens, or a personal protection article, or an article comprising a portion having a thickness in the range of 0.5 millimeter to 2 centimeter, or of 0.1 to 10 millimeter.

Embodiment 20

A method for the quantitation of a carboxylic acid end group in a polymer soluble in a halogenated solvent, the method comprising:

derivatizing a carboxylic acid end group in the polymer with 2-chloro-1,3,2-benzodioxaphosphole to provide a derivatized end group in the presence of a known amount of a reactive standard; and quantifying the amount of the derivatized end group via $^{31}$P nuclear magnetic resonance spectroscopy relative to the reactive standard.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments," "an embodiment," and so forth, means that a particular element described in connection with the embodiment is included in at least one embodiment described herein, and may or may not be present in other embodiments. In addition, it is to be understood that the described elements can be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. Unless substituents are otherwise specifically indicated, each of the foregoing groups can be unsubstituted or substituted, provided that the substitution does not significantly adversely affect synthesis, stability, or use of the compound. "Substituted" means that the compound, group, or atom is substituted with at least one (e.g., 1, 2, 3, or 4) substituents instead of hydrogen, where each substituent is independently nitro (—NO$_2$), cyano (—CN), hydroxy (—OH), halogen, thiol (—SH), thiocyano (—SCN), C$_{1-6}$ alkyl, C$_{2-6}$ alkenyl, C$_{2-6}$ alkynyl, C$_{1-6}$ haloalkyl, C$_{1-9}$ alkoxy, C$_{1-6}$ haloalkoxy, C$_{3-12}$ cycloalkyl, C$_{5-18}$ cycloalkenyl, C$_{6-12}$ aryl, C$_{7-13}$ arylalkylene (e.g., benzyl), C$_{7-12}$ alkylarylene (e.g., toluyl), C$_{4-12}$ heterocycloalkyl, C$_{3-12}$ heteroaryl, C$_{1-6}$ alkyl sulfonyl (—S(=O)$_2$-alkyl), C$_{6-12}$ arylsulfonyl (—S(=O)$_2$-aryl), or tosyl (CH$_3$C$_6$H$_4$SO$_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the compound or group, including those of any substituents.

While particular embodiments have been described, alternatives, modifications, variations, improvements, and substantial equivalents that are or presently unforeseen can arise to applicants or others skilled in the art. Accordingly, the appended claims as filed and as they can be amended are intended to embrace all such alternatives, modifications variations, improvements, and substantial equivalents.

What is claimed is:

1. An interfacial process for preparing a poly(aliphatic ester-carbonate), the process comprising:
   providing an initial polymerization reaction mixture comprising an $C_{6-20}$ aliphatic dicarboxylic acid, a bisphenol, an alkali hydroxide, and optionally a catalyst in a solvent system comprising water and an immiscible organic solvent;
   adding an initial portion of a carbonyl dihalide over a first time period while maintaining the reaction at a first pH from 7 to less than 8; and
   adding a second portion of the carbonyl dihalide over a second, subsequent time period while maintaining the reaction pH at a second pH from 9 to 12, to provide a product polymerization mixture comprising the poly(aliphatic ester-carbonate),
   wherein the amount of the alkali hydroxide in the initial polymerization reaction mixture is an amount effective to increase the fraction of the first time period at a measured pH of 7 to 8 compared to the same reaction mixture with a higher amount of the alkali hydroxide in the initial polymerization mixture, and
   wherein no additional alkali hydroxide is added after providing the initial polymerization reaction mixture and before adding the initial portion of the carbonyl dihalide, or after the adding the initial portion of the carbonyl dihalide.

2. The process of claim 1, wherein the fraction of the first time period at the measured pH of 7 to 8 is at least 70% of the total duration of the first time period.

3. The process of claim 1, wherein the amount of the alkali hydroxide in the initial polymerization reaction mixture is an amount effective to provide the poly(aliphatic ester-carbonate) having a —COOH end group content of less than 75 parts per million by weight, as measured by $^{31}P$ nuclear magnetic resonance spectroscopy.

4. The process of claim 1, wherein
   the first time period is more than 9 minutes; and
   the second time period is 10 minutes or greater.

5. The process of claim 1, wherein
   the first pH is from 7.0 to 8.0; and
   the second pH is from 9.7 to 10.9.

6. The process of claim 1, wherein
   the initial portion of the carbonyl dihalide is 28 to 50% of the total amount of the initial portion of the carbonyl dihalide and the second portion of the carbonyl dihalide used in the process.

7. The process of claim 1, wherein the providing the initial reaction mixture comprises combining the $C_{6-20}$ aliphatic dicarboxylic acid, the bisphenol, the water, the alkali hydroxide, the immiscible organic solvent, and optionally the catalyst before adding the initial portion of the carbonyl dihalide.

8. The process of claim 7, comprising pre-combining the $C_{6-20}$ aliphatic dicarboxylic acid, the bisphenol, the water, the immiscible organic solvent, and optionally the catalyst; and then adding the alkali hydroxide before adding the initial portion of the carbonyl dihalide.

9. The process of claim 1, wherein the providing the initial polymerization reaction mixture comprises pre-combining the bisphenol, the water, the immiscible organic solvent, and optionally the catalyst; and then adding the $C_{6-20}$ aliphatic dicarboxylic acid and the alkali hydroxide before adding the initial portion of the carbonyl dihalide.

10. The process of claim 1, wherein the providing the initial polymerization reaction mixture comprises combining the bisphenol, the water, the alkali hydroxide, the immiscible organic solvent, and optionally the catalyst; and then adding the $C_{6-20}$ aliphatic dicarboxylic acid with the addition of the initial portion of the carbonyl dihalide.

11. The process of claim 9, wherein
   the $C_{6-20}$ aliphatic dicarboxylic acid is added as a solid or as a slurry separately from the alkali hydroxide; or
   the $C_{6-20}$ aliphatic dicarboxylic acid is pre-dissolved in water with the alkali hydroxide, and then added.

12. The process of claim 1, wherein
   the $C_{6-20}$ aliphatic dicarboxylic acid is azelaic acid, sebacic acid, or dodecanedioic acid;
   the bisphenol is bisphenol A;
   the alkali hydroxide is sodium hydroxide; and
   the carbonyl dihalide is carbonyl dichloride.

13. The process of claim 1, wherein
   the $C_{6-20}$ aliphatic dicarboxylic acid is present in the initial polymerization reaction mixture in an amount of 5 to 12 mole percent, based on the moles of the bisphenol.

14. The process of claim 1, wherein the catalyst is a tertiary amine catalyst, and is present in the initial polymerization reaction mixture in an amount of 0.75 to 3.0 mole percent, based on the moles of the bisphenol.

15. A poly(aliphatic ester-carbonate) made by the process of claim 1.

16. The poly(aliphatic ester-carbonate) of claim 15, having
   a weight average molecular weight of 10,000 to 50,000 Dalton, as measured by gel permeation chromatography, based on bisphenol A polycarbonate standards;
   5 to 12 mole percent of units derived from the $C_{6-20}$ aliphatic dicarboxylic acid;
   a glass transition temperature of 110 to 145° C.;
   a decrease in weight average molecular weight of less than 30% after heat aging a molded sample for 4 weeks at 85° C. and 85% humidity;
   a decrease in weight average molecular weight of less than 60% after heat aging a molded sample for 8 weeks at 85° C. and 85% humidity; and
   a —COOH end group content of less than 75 parts per million by weight, as measured by $^{31}P$ nuclear magnetic resonance spectroscopy.

17. A polymer composition comprising the poly(aliphatic ester-carbonate) of claim 15, and further comprising an additive.

18. An article subject to conditions of heat and humidity, wherein the article comprises the poly(aliphatic ester-carbonate) of claim 15.

19. The process of claim 1, further comprising quantifying carboxylic acid end group content in the poly(aliphatic ester-carbonate), wherein the quantifying comprises:
   derivatizing a carboxylic acid end group in the polymer with 2-chloro-1,3,2-benzodioxaphosphole to provide a derivatized end group in the presence of a known amount of a reactive standard; and quantifying the amount of the derivatized end group via $^{31}$P nuclear magnetic resonance spectroscopy relative to the reactive standard.

\* \* \* \* \*